United States Patent [19]

Chuang et al.

[11] Patent Number: 5,210,319
[45] Date of Patent: May 11, 1993

[54] ONE STEP CARBOXYLIC ACID PRODUCTION PROCESS

[76] Inventors: Karl T. Chuang, Dept. of Chemical Engineering, University of Alberta, Edmonton, Canada, T6G 2G6; Long Fu, 11642 - 76 Ave., Edmonton, AB, Canada, T6G 0K8

[21] Appl. No.: 844,195

[22] Filed: Mar. 2, 1992

[51] Int. Cl.⁵ .............................. C07C 51/16
[52] U.S. Cl. .................................... 562/546
[58] Field of Search .............. 562/546, 519, 522

[56] References Cited

U.S. PATENT DOCUMENTS

| | | | |
|---|---|---|---|
| 4,499,301 | 2/1985 | Murib | 562/546 |
| 4,788,334 | 11/1988 | Burke | 562/522 |
| 4,792,620 | 12/1988 | Pavlik et al. | 562/519 X |
| 4,837,360 | 6/1989 | Kadowaki et al. | 562/546 |
| 4,861,912 | 8/1989 | Drent et al. | 562/522 X |
| 4,902,822 | 2/1990 | Drent | 562/522 X |
| 5,149,868 | 9/1992 | Drent | 562/522 X |

Primary Examiner—Arthur C. Prescott
Attorney, Agent, or Firm—Francis W. Lemon

[57] ABSTRACT

A single step process for the oxidation of an olefin to its respective $\alpha$-,$\beta$-unsaturated carboxylic acid is described. The olefin in vapor form is reacted with oxygen in the presence of a noble metal oxidation catalyst on a hydrophobic support and an aqueous solvent.

10 Claims, 1 Drawing Sheet

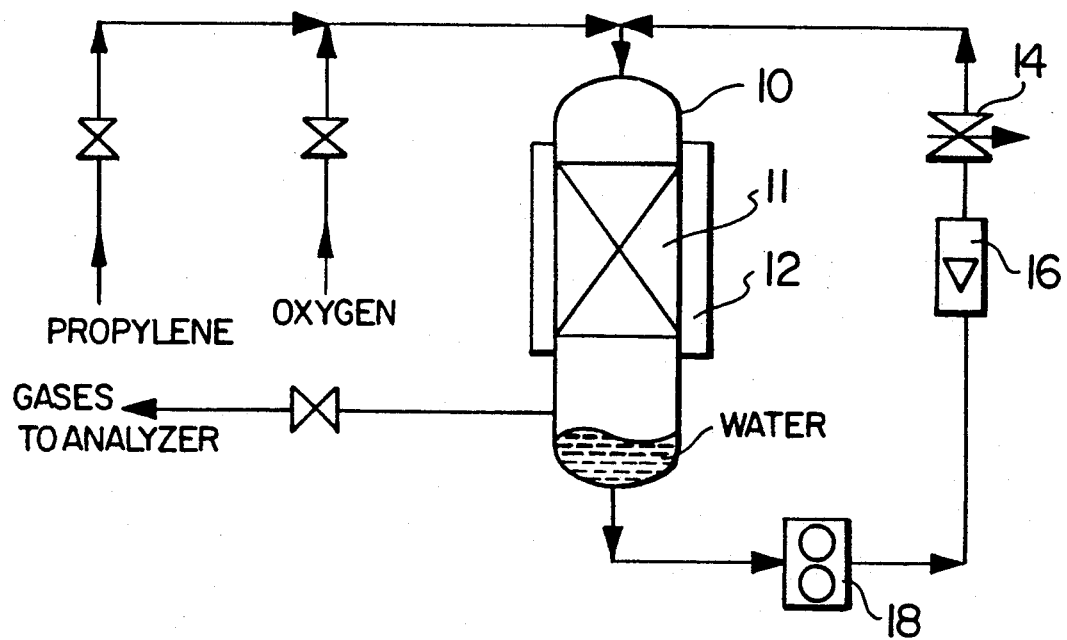

ONE STEP CARBOXYLIC ACID PRODUCTION PROCESS

BACKGROUND OF THE INVENTION

1. Field of the Invention

This invention relates to the oxidation of olefins to α-β-unsaturated carboxylic acids, and in particular to an improved single step process for the oxidation of propylene to acrylic acid.

Acrylic acid and esters are a highly versatile series of monomers that provide performance characteristics to thousands of polymer formulations. They are flammable, reactive, volatile liquids based on an alpha, beta-unsaturated carboxyl structure. They polymerize readily, yet can be stored and transported safely through the use of very low concentrations of inhibitors. As a consequence of these desirable qualities, they have become an important commodity chemical with a very high growth rate.

2. Description of the Prior Art

Production of acrylic acid and esters has been the subject of intense technological investigation leading to a great variety of processes. The dominant route that has evolved from this work is the catalytic vapour phase oxidation of propylene in two stages, firstly to acrolein vapour and then to acrylic acid vapour using several different catalyst systems followed by aqueous absorption.

Many attempts have been made to simplify the process by combining the oxidation steps. Other investigators have reported on their efforts to include both oxidation steps and the absorption step in a single trickle-bed reactor. Unfortunately, these methods have either produced low yields of acrylic acid based on propylene consumed (low selectivity) or impractical reaction rates.

The oxidation of propylene to acrylic acid in one step employing a palladium metal catalyst supported on carbon black is described in U.S. Pat. No. 3,624,147. However, this process is characterized by yields of 60% or less, based on the amount of propylene converted, operating temperatures generally in excess of 90° C., and elevated pressures. Moreover, substantial amounts of $CO_2$ are reported as undesired by-products, as well as low reaction rates.

A similar process is reported in *J. Catal.*, 173 (1972) by Seiyama et al., in which palladium black and palladium-activated charcoal were employed for converting propylene to acrylic acid. However, only a stoichiometric, non-catalytic conversion, based on the palladium metal, is taught, thus providing an even less effective method than in the above U.S. Pat.

A different approach using a similar catalyst is reported in EPO published application 145 467 A3. In this process, the palladium catalyst is first activated by preliminary high temperature contact with an olefin, e.g. propylene. Gaseous oxygen and propylene are then passed through the catalyst bed along with a liquid aqueous media which removes the acrylic acid as it is produced, carrying it downwards for recovery. The catalyst is active in promoting the reaction at temperatures as low as 25° C. with high selectivity. Moreover, the undesired by-product, $CO_2$, is virtually eliminated.

Even higher selectivities are claimed for this process in EPO published application 145 468 where certain surfactants are used in combination with a co-surfactant such as n- or t- butyl alcohol. Similar improvement claims are made in EPO published application 145 469 when a free radical inhibitor such as butylated hydroxytoluene is added to the reactants.

Still another approach to the problem is shown in U.S. Pat. No. 3,792,086 where palladium is combined with phosphoric acid. This catalyst is claimed to constitute a significant advance in the art in that high selectivity is achieved, but the catalyst efficiency deteriorates rapidly due to the formation of a tar that coats the catalyst thus impeding efficient contact with the reactants.

U.S. Pat. No. 3,947,495 claims to have overcome this problem by adding a sulphur modifier. The addition of sulphur (in any one of several forms) apparently inhibits tar formation thus improving both reaction rates and catalyst stability.

U.S. Pat. No. 4,499,307 reveals still another approach to the problem, whereby a solid acid consisting of mixed metal oxides is substituted for phosphoric acid in the catalyst. The catalytically effective metal in this catalyst can be one of a group of noble metals including palladium, gold, and silver, with the preferred composition containing palladium and gold. High selectivities are claimed for this process.

All of the above methods for converting propylene to acrylic acid in a single stage oxidation step suffer from the defect of either low selectivity (i.e. low yield of acrylic acid based on propylene consumed) or low catalyst efficiency (i e low production in terms of grams of acrylic acid produced per gram of palladium per hour) or both.

SUMMARY OF THE INVENTION

It is well documented both in the literature and from our own tests that selectivity to acrylic acid increases as temperature decreases, whereas both conversion and yield decline. It has also been suggested that water plays an important role in the reaction as well as being one of the products of the reaction.

Although some of these prior art processes exhibit high selectivity, reaction rates are generally too low for any practical applications. These rates are several orders of magnitude lower than those reported for the vapour phase reactions. The reason for the low catalyst activity can be attributable to the fact that the reactions are limited by the mass transfer of the reactants to the catalyst surface. Clearly, when the catalyst (Pd/C) is exposed to liquid water, it becomes wet due to the capillary effect, and therefore the gaseous reactants must dissolve in the liquid in order to reach the Pd surfaces. Since propylene and oxygen are sparsely soluble in aqueous solutions, the rate-determining step is the mass transfer of reactants to the reaction sites. This limitation cannot be removed by changing reaction temperature. Increasing pressure results in higher gas solubility, but the pressure is limited by the liquefaction of propylene. It appears that the process improvement can only come from the redesign of the catalyst to overcome the mass transfer limitation.

To overcome the mass transfer limitation, the applicants propose a relatively simple solution which can be rapidly developed for industrial applications.

It is postulated that when conventional catalyst is exposed to aqueous solutions, capillary condensation takes place until it reaches thermodynamic equilibrium dictated by the Kelvin equation [1]:

$$ln\ (P/P_o) = 2V\gamma \cos\theta/(rRT) \qquad [1]$$

where r is the radius of the capillary, V is the molar volume of the liquid and $\tau$ the surface tension. Equation [1] indicates that for values of the contact angle less than 90°, liquid condenses in the capillary at a pressure P less than the saturated pressure $P_o$ at temperature T. For conventional catalyst supports, the materials are hydrophilic and the contact angle with an aqueous solution would be close to zero. Thus the whole catalyst is wet when exposed to the liquid. The equation also implies that increasing contact angle reduces pore condensation. In the presence of a liquid, the P is equal to $P_o$ and if a hydrophobic material with a $\theta$ greater than 90° ($\cos \tau$ becomes negative) is selected as a catalyst support, its pores will remain dry and accessible to the gaseous reactants. In this way the concentration of the reactants at the reaction sites in the pores is increased by a factor of $10^4$, roughly the Henry's law constant for oxygen. In addition the rate of diffusion in the gas phase is about 1,000 to 10,000 times higher than that in the liquid phase. Accordingly the combination of carrying out the oxidation in the vapour phase and using a hydrophobic catalyst support is employed.

Thus, according to the invention, a single step process for the oxidation of a C3 to C6 olefin to its respective $\alpha, \beta$-unsaturated carboxylic acid is provided, comprising reacting the olefin in vapour form, with oxygen in the presence of a noble metal oxidation catalyst on a hydrophobic support and an aqueous solvent to absorb the acid as it forms, to facilitate recovery thereof.

For example, if the olefin is propylene, isobutylene or butene-1, the respective acids produced are acrylic acid, methacrylic acid and crotonic acid. In general, olefins of 3 to 6 carbon atoms may be oxidized according to the invention. The specific description of the invention which follows describes the oxidation of propylene to acrylic acid, as this specific example is perhaps the most important commercially.

BRIEF DESCRIPTION OF THE DRAWING

The FIGURE is a schematic illustration of a typical apparatus used to carry out the method according to the invention.

DETAILED DESCRIPTION OF THE PREFERRED EMBODIMENT

The experimental proofs of concept were conducted in an apparatus of the type illustrated in the figure. As seen in the figure, a pressurized packed trickle bed reactor 10 made from type 316 stainless steel contains a 40 cc catalyst bed 11.

The proposed gas-liquid-solid reactor can be described mathematically. The reaction mechanism involves several steps, some of them interrelated. Gas phase diffusion of reactants to the catalyst sites, reactions to form acrylic acid and other side products, stability of the acid, gas and liquid distribution over catalyst particles and mass transfer of the acid into the aqueous solution should all be taken into account in the model.

Specifically, the catalyst is a hydrophobic oxidation catalyst containing a noble metal (Pt, Pd, Rh, Ru, or Ir) and combinations thereof, on a hydrophobic support e.g. styrene-divinylbenzene co-polymer, fluorinated carbon and silicalite. See U.S. Pat. No. 5,009,872, the disclosure of which is incorporated herein by reference.

It is also important to ensure that the contact angle $\theta$ is greater than 90° for the liquid solution to be contacted. The surface area should be high enough so that sufficient metal catalyst can be deposited with good dispersion, say in the range of 50–800 m²/g.

The bed packing is a mixture of the hydrophobic catalyst and an inert support. For better mass transfer of acrylic acid vapour into the aqueous solution, a hydrophilic support is preferred.

The inert hydrophilic support can range from 1/32" to 2", is typically ¼ inch ceramic Raschig rings, although other conventional packing materials such as glass spheres, ceramic saddles or ordered bed packings could also be used.

The packing is made by coating the rings with a small quantity of fluorinated carbon and Teflon ® to provide a hydrophobic support and by impregnating the support with noble metal salt e.g. $H_2PtCl_6$ dissolved in ethanol. The resulting catalyst is then heated in air at 200° C. and reduced in $H_2$ at the same temperature overnight to activate the catalyst.

A heating jacket 12 is provided to control the reaction temperature. Reaction temperatures in the range of 75° to 150° C. are contemplated.

Suitable reaction pressures are in the range of 400 KPa to the liquefaction pressure of the olefin.

The use of liquid water in a trickle-bed reactor enhances the process in two ways:
1) it rapidly removes the exothermic heat of reaction, thus reducing the probability of localized high temperatures
2) it keeps the catalyst surface clean, ensuring high reaction rate.

In operation, propylene is first vapourized by a vapourizer 18 and then directed, along with oxygen (supplied as air, although molecular oxygen could also be used), to the reactor 10. Liquid water is also directed to the reactor. The reactants are then introduced at the top of the reactor and flowed Concurrently downward to avoid flooding of the reactor. The acrylic acid product is absorbed by the water as it forms, and is removed at the bottom of the reactor. Other aqueous solvents could also be employed, such as those containing acrylic acid stabilizers to avoid polymerization.

The flow rate of the reactants was controlled by Mass Flow Controllers, not shown. A micro-gear pump 12 was used for recycling water and liquid product. The flow rate was controlled by a needle valve 14 and measured by a rotameter 16. The pressure of the system was controlled by a Back Pressure Regulator (not shown). The quantitative analysis of the reactants and products was carried out by Gas Chromatography and the qualitative analysis was conducted by GC-Mass spectroscopy.

Several catalyst combinations have been tested. Table 1 below shows the results for the active metal(s) supported on styrene-divinylbenzene copolymer. Typical superficial space velocity of 3060 h$^{-1}$ was maintained. Oxygen was supplied as air to provide a molar ratio of $O_2:C_3^-$ of 1.5.

Typical results from other prior patents are summarized at the bottom of Table 1. It can be seen from the table that, while similar selectivities have been reported, yields are only a fraction of those achieved using hydrophobic catalysts according to the invention.

TABLE 1

| Run No. | Catalyst | Temp °C. | Pressure (kPa) | $C_3$ Conversion % | Selectivity % | Yield (g/g Pd·h) | Reference Number |
|---|---|---|---|---|---|---|---|
| 1 | 10% Pd/SDB | 120 | 1,060 | 47 | 87.0 | 14.85 | |
| 2 | " | 120 | 920 | 40 | 85.6 | 12.67 | |
| 3 | " | 120 | 790 | 36 | 84.0 | 11.34 | |
| 4 | " | 141 | 920 | 72.5 | 81.9 | 22.17 | |
| 5 | " | 130 | 920 | 68.0 | 81.9 | 21.08 | |
| 6 | 5% Pd/SDB | 140 | 920 | 43.3 | 82.5 | 26.91 | |
| 7 | 1% Pd/SDB | 139 | 920 | 25.2 | 79.6 | 40.81 | |
| 8 | 2% Pd + 0.4% Pt/SDB | 140 | 920 | 18.6 | 81.6 | 28.65 | |
| 9 | 6% Pd + 2% Ru/SDB | 140 | 920 | 32.64 | 82.3 | 16.24 | |
| Comparative Results from other Patents | | | | | | | |
| | 10% Pd/Carbon | 65 | 790 | — | 89.9 | 2.33 | EPO 145,467 |
| | 10% Pd/Carbon | 65 | 790 | — | 87.9 | 1.19 | EPO 145,468 |
| | 10% Pd/Carbon | 65 | 790 | — | 93.2 | 3.36 | EPO 145,468 |
| | 1% PD 2% Au 16% $H_3PO_4$ + $(C_6H_5)_3$ SCl on Silica | 207 | — | 38.1 | 81.0 | 5.53 | UK 1,036,375 |
| | 1.3% Pd 0.5% Au/ Solid Acid | 152 | — | 17.0 | 73.5 | 0.767 | US 4,499,301 |
| | Pd Black | 55 | — | — | 98.0 | 0.96 | UK 1,035,147 |
| | 2% Pd 0.5% Cu/ $SiO_2$ | 155 | — | — | 75.2 | 0.85 | UK 1,036,375 |

We claim:

1. A single step process for the oxidation of a C3 to C6 olefin to its respective $\alpha$-,$\beta$-unsaturated carboxylic acid, comprising reacting the olefin in vapour form, with oxygen in the presence of a noble metal oxidation catalyst on a hydrophobic support and an aqueous solvent.

2. A process according to claim 1, wherein the process is carried out with stoichiometric amounts of olefin and oxygen required to produce the carboxylic acid.

3. A process according to claim 2, wherein the reaction temperature is in the range of 75° to 150° C.

4. A process according to claim 3, wherein the reaction pressure is in the range of 400 KPa to the liquefaction pressure of the olefin.

5. A process according to claim 4, wherein the oxygen is supplied as air.

6. A process according to claim 5, wherein the aqueous solvent is water.

7. A process according to claim 6, wherein the noble metal oxidation catalyst is selected from the group consisting of Pt, Pd, Rh, Ru, Ir and combinations thereof.

8. A process according to claim 7, wherein the hydrophobic support is selected from the group consisting of styrene-divinylbenzene copolymer, fluorinated carbon and silicalite.

9. A process according to claim 8, wherein the catalyst contact angle is >90°.

10. A process according to claim 9, wherein the olefin is propylene and the carboxylic acid is acrylic acid.

* * * * *